(12) United States Patent
Kulkarni et al.

(10) Patent No.: US 12,106,855 B2
(45) Date of Patent: Oct. 1, 2024

(54) TECHNIQUES FOR TREATING MENTAL HEALTH DISORDERS USING DIGITAL THERAPEUTICS

(71) Applicant: The Joan and Irwin Jacobs Technion-Cornell Institute, New York, NY (US)

(72) Inventors: Prathamesh Kulkarni, New York, NY (US); Wilfred Krenn, St. Louis, MO (US)

(73) Assignee: The Joan and Irwin Jacobs Technion-Cornell Institute, New York, NY (US)

( * ) Notice: Subject to any disclaimer, the term of this patent is extended or adjusted under 35 U.S.C. 154(b) by 350 days.

(21) Appl. No.: 17/151,400

(22) Filed: Jan. 18, 2021

(65) Prior Publication Data
US 2021/0335498 A1    Oct. 28, 2021

Related U.S. Application Data

(60) Provisional application No. 63/014,990, filed on Apr. 24, 2020.

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/7267* (2013.01); *A61B 5/7275* (2013.01);
(Continued)

(58) Field of Classification Search
CPC ........ G16H 50/20; G16H 10/60; G16H 20/70; G16H 50/70
See application file for complete search history.

(56) References Cited

U.S. PATENT DOCUMENTS 10,477,342 B2 * 11/2019 Williams ........... A61B 5/02055
10,943,407 B1    3/2021 Morgan et al.
(Continued)

FOREIGN PATENT DOCUMENTS

CN    110383389 A * 10/2019 ............. G06N 20/00
JP    2019527073 A    9/2019
(Continued)

OTHER PUBLICATIONS

Benjamin Shickel et al., Automatic Detection and Classification of Cognitive Distortions in Mental Health Text, Sep. 23, 2019, arXiv:1909.07502v2 (Year: 2019).*
(Continued)

*Primary Examiner* — Evangeline Barr
(74) *Attorney, Agent, or Firm* — M&B IP Analysts, LLC

(57) ABSTRACT

A system and method for developing a treatment plan using multi-stage machine learning. A method includes determining a treatment plan for a patient based on at least one mental health disorder of a patient, wherein the treatment plan includes a plurality of digital therapeutics exercise tasks, wherein each digital therapeutics exercise task is selected from among a category of digital therapeutics exercise tasks corresponding to a type of mental health disorder of the at least one mental health disorder of the patient; and administering treatment to the patient by prescribing the treatment plan to the patient and causing data for administering the treatment plan to a user device of the patient.

18 Claims, 6 Drawing Sheets

(51) Int. Cl.
  *G06F 18/214* (2023.01)
  *G06N 20/00* (2019.01)
  *G16H 10/20* (2018.01)
  *G16H 10/60* (2018.01)
  *G16H 20/70* (2018.01)
  *G16H 50/30* (2018.01)
  *G16H 50/70* (2018.01)

(52) U.S. Cl.
  CPC .......... *G06F 18/214* (2023.01); *G06N 20/00* (2019.01); *G16H 10/20* (2018.01); *G16H 10/60* (2018.01); *G16H 20/70* (2018.01); *G16H 50/30* (2018.01); *G16H 50/70* (2018.01)

(56) References Cited

U.S. PATENT DOCUMENTS

| | | | |
|---|---|---|---|
| 2015/0025997 A1 | 1/2015 | Tilenius et al. | |
| 2015/0120283 A1* | 4/2015 | Lehman | G06F 40/253 704/9 |
| 2015/0125832 A1 | 5/2015 | Tran | |
| 2015/0370993 A1* | 12/2015 | Moturu | G16H 50/50 703/6 |
| 2017/0000422 A1 | 1/2017 | Moturu et al. | |
| 2017/0132395 A1* | 5/2017 | Futch | G06Q 40/08 |
| 2018/0176727 A1 | 6/2018 | Williams | |
| 2018/0307801 A1 | 10/2018 | Hardee et al. | |
| 2019/0043610 A1* | 2/2019 | Vaughan | G16H 50/20 |
| 2019/0043618 A1 | 2/2019 | Vaughan et al. | |
| 2019/0110753 A1 | 4/2019 | Zhang et al. | |
| 2019/0171438 A1 | 6/2019 | Franchitti | |
| 2019/0182193 A1* | 6/2019 | Moskowitz | G16H 80/00 |
| 2019/0189259 A1* | 6/2019 | Clark | G16H 10/60 |
| 2019/0252080 A1* | 8/2019 | Liu | G16H 80/00 |
| 2019/0295703 A1 | 9/2019 | Das et al. | |
| 2020/0023157 A1* | 1/2020 | Lewis | A61B 5/02055 |
| 2020/0082927 A1* | 3/2020 | Hernandez | A61M 21/02 |
| 2020/0303056 A1 | 9/2020 | Sullivan | |
| 2020/0327977 A1 | 10/2020 | Moskowitz | |
| 2020/0330019 A1 | 10/2020 | Brown et al. | |
| 2020/0335191 A1 | 10/2020 | Brown et al. | |
| 2020/0350076 A1 | 11/2020 | Brown et al. | |
| 2021/0074178 A1 | 3/2021 | Ilan et al. | |
| 2021/0090733 A1* | 3/2021 | Dibari | G16H 15/00 |
| 2022/0230731 A1 | 7/2022 | Gilutz et al. | |

FOREIGN PATENT DOCUMENTS

| | | | | |
|---|---|---|---|---|
| KR | 20190023025 A | * | 3/2019 | |
| WO | WO-2017106770 A1 | * | 6/2017 | .......... A61B 5/0022 |
| WO | WO-2018148365 A1 | * | 8/2018 | ............. A61B 5/168 |

OTHER PUBLICATIONS

International Search Report and Written Opinion of International Searching Authority for PCT/US2021/050356, ISA/RU, Moscow, Russia, Dated: Mar. 19, 2021.
International Search Report and Written Opinion of International Searching Authority for PCT/IB2021/050355, ISA/RU, Moscow, Russia, Dated: Mar. 19, 2021.
International Preliminary Report on Patentability for PCT Application No. PCT/IB2021/050355 dated Oct. 25, 2022. The International Bureau of WIPO.
International Preliminary Report on Patentability for PCT Application No. PCT/IB2021/050356 dated Oct. 25, 2022. The International Bureau of WIPO.

* cited by examiner

TECHNIQUES FOR TREATING MENTAL HEALTH DISORDERS USING DIGITAL THERAPEUTICS

CROSS-REFERENCE TO RELATED APPLICATIONS

This application claims the benefit of U.S. Provisional Application No. 63/014,990 filed on Apr. 24, 2020, the contents of which are hereby incorporated by reference.

TECHNICAL FIELD

The present disclosure relates generally to rehabilitation of mental health issues using digital therapeutics, and more specifically to machine learning techniques enabling such rehabilitation using digital therapeutics.

BACKGROUND

Many people face challenges with mental health disorders. Mental health disorders may have particularly negative effects on professionals that work in fields where stress is high and cognitive abilities are crucial to high quality, efficient work production. For example, legal professionals face high demand for production of work requiring sharp memory and critical thinking. These challenges may affect performance, which in turn may further contribute to exacerbating or initiating mental health issues such as anxiety and depression.

Digital therapeutics are software-based treatments that have direct impacts on illnesses or diseases. Digital therapeutics provide solutions for preventing, managing, or treating health conditions, either alone or in combination with non-digital treatments.

It would therefore be advantageous to provide new solutions for applying digital therapeutics for the rehabilitation of mental health disorders.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for developing a treatment plan using multi-stage machine learning. The method comprises: determining a treatment plan for a patient based on at least one mental health disorder of a patient, wherein the treatment plan includes a plurality of digital therapeutics exercise tasks, wherein each digital therapeutics exercise task is selected from among a category of digital therapeutics exercise tasks corresponding to a type of mental health disorder of the at least one mental health disorder of the patient; and administering treatment to the patient by prescribing the treatment plan to the patient and causing data for administering the treatment plan to a user device of the patient.

Certain embodiments disclosed herein also include a non-transitory computer readable medium having stored thereon causing a processing circuitry to execute a process, the process comprising: determining a treatment plan for a patient based on at least one mental health disorder of a patient, wherein the treatment plan includes a plurality of digital therapeutics exercise tasks, wherein each digital therapeutics exercise task is selected from among a category of digital therapeutics exercise tasks corresponding to a type of mental health disorder of the at least one mental health disorder of the patient; and administering treatment to the patient by prescribing the treatment plan to the patient and causing data for administering the treatment plan to a user device of the patient.

Certain embodiments disclosed herein also include a system for developing a treatment plan using multi-stage machine learning. The system comprises: a processing circuitry; and a memory, the memory containing instructions that, when executed by the processing circuitry, configure the system to: determine a treatment plan for a patient based on at least one mental health disorder of a patient, wherein the treatment plan includes a plurality of digital therapeutics exercise tasks, wherein each digital therapeutics exercise task is selected from among a category of digital therapeutics exercise tasks corresponding to a type of mental health disorder of the at least one mental health disorder of the patient; and administer treatment to the patient by prescribing the treatment plan to the patient and causing data for administering the treatment plan to a user device of the patient.

BRIEF DESCRIPTION OF THE DRAWINGS

The subject matter disclosed herein and other objects, features, and advantages of the disclosed embodiments will be apparent from the following detailed description taken in conjunction with the accompanying drawings.

DETAILED DESCRIPTION

Figure 1:
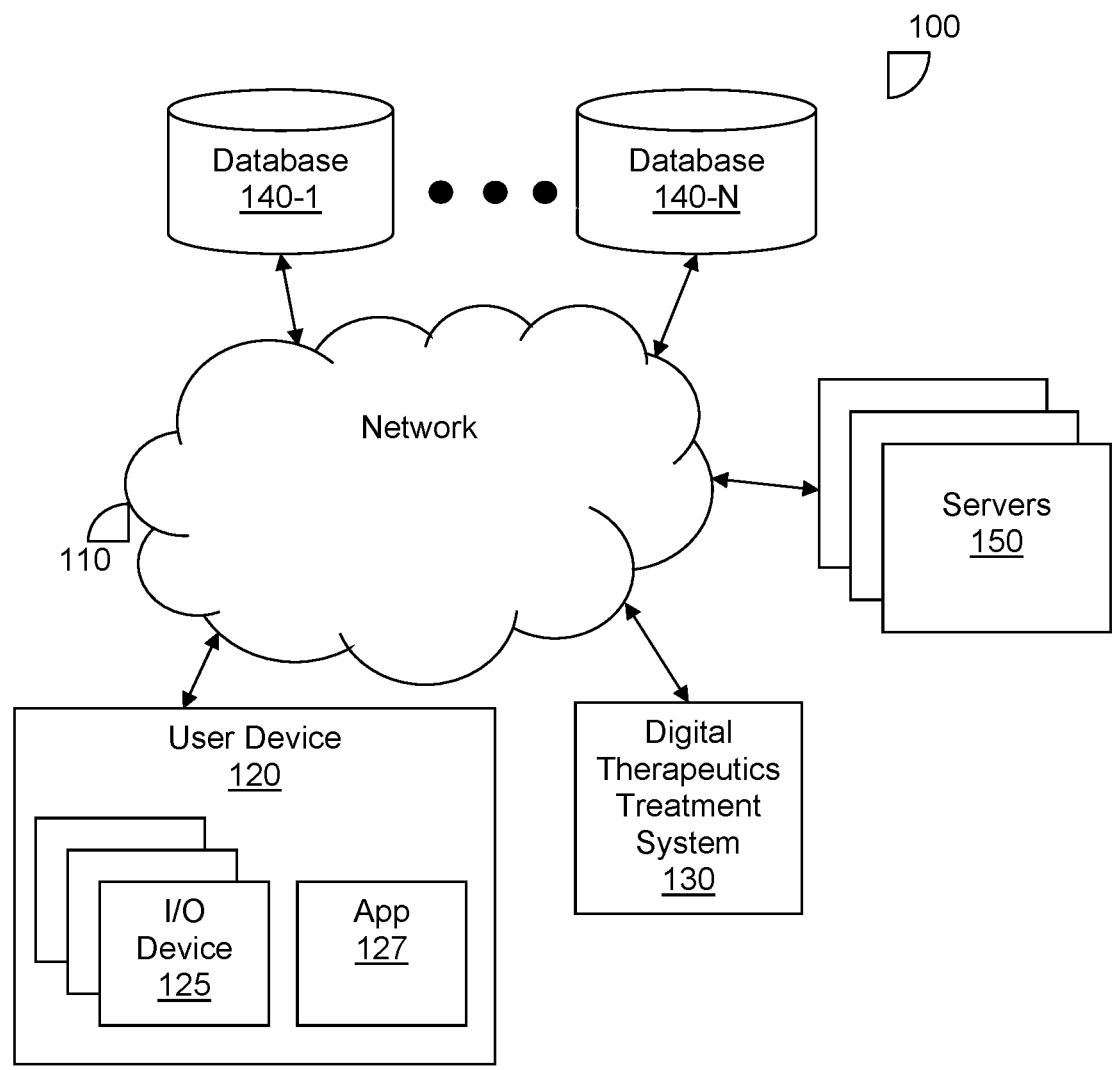
FIG. 1 is a network diagram utilized to describe various disclosed embodiments.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

It has been identified that assigning specific mental health exercises to patients having particular types of cognitive distortions can alleviate the effects of those cognitive distortions and symptoms of underlying mental health disorder. Additionally, the information needed to diagnose patients with mental health disorders can be more readily obtained by guiding patients through use of social media or other platforms where users create content that may reflect their mental state. To this end, the disclosed embodiments provide techniques for treating mental health disorders using specific sets of digital therapeutics exercise tasks.

Additionally, it has been identified that the types of content provided via user-created content platforms may be more effectively and rapidly processed via automated solutions as compared to manual analysis of content by medical health professionals. In particular, the sheer volume of content may hinder treatment by medical health professionals where automated solutions would allow for effectively providing treatment. To this end, the disclosed embodiments provide techniques for identifying mental health disorders of users and determining treatments for those mental health disorders using machine learning that allows for automating diagnosis and treatment. Further, in order to improve accuracy of the machine learning models applied for these identifications and determinations, the disclosed embodiments include multi-stage, synergistic machine learning techniques that provide more accurate diagnoses and corresponding treatments as compared to other machine learning schemas.

The various disclosed embodiments also include a method for treatment of mental health disorders using digital therapeutics. A set of digital therapeutics is determined for a patient based on a type of mental health disorder the patient has been diagnosed with. The set of digital therapeutics includes digital therapeutics selected from a category of digital therapeutics corresponding to the type of mental health disorder. In an embodiment, the digital therapeutics include assignment of digital therapeutics exercise tasks via a user interface.

In some embodiments, the treatment may further include determining a diagnosis of a mental health disorder and applying digital therapeutics based on the diagnosis. To this end, the treatment may include applying one or more of the machine learning models to data related to user activity in order to determine the diagnosis. The digital therapeutics to be applied are determined based on the diagnosis and then applied, for example, via a user interface of a user device used by the patient. The diagnoses and treatment plan may be updated, for example, periodically or when new data is provided. The updated diagnoses may be utilized to provide targeted exercises based on portions of the diagnosis (e.g., the treatment plan may be updated to include depression-related exercises when depression scores above a threshold are determined).

In some embodiments, the set of digital therapeutics are realized as content provided via a specific diagnostic-based channel with a specific goal. The channel may be selected (e.g., by a user), and may be provided as recommendations. The channel may be limited to users who have been assigned or recommended that channel such that all users using the channel have similar symptomology in the form of the same or related mental health disorder, occupation, position, combinations thereof, and the like. By providing the treatment plan in a channel with other users having the same or related mental health disorders, each user is provided with a relevant peer support experience. Further, the user's communication with other users in the peer group may be utilized as additional data which can be analyzed (for example, using machine learning techniques as described herein) in order to further improve assessment and, consequently, to improve accuracy of treatment plan generation.

The various disclosed embodiments also include a method and system for treating mental health disorders using machine learning. Features are input to a digital therapeutics treatment machine learning model, which outputs data indicating digital therapeutics to be prescribed to a user for treatment. The prescribed digital therapeutics include a set of digital therapeutics exercise tasks. In an embodiment, the prescribed digital therapeutics output by the digital therapeutics machine learning model are administered to the user, for example, via a user interface of a user device.

The input features include at least an identifier of one or more cognitive distortions of the user, and may further include data related to prior digital therapeutics prescribed to the user. The cognitive distortion identifiers, the data related to prior digital therapeutics, or both, are determined by applying one or more machine learning models to data related to interactions of the user with a digital therapeutics platform. The interactions may include, but are not limited to, posts of the user, responses of the user, both, and the like.

In an embodiment, machine learning is performed via a hierarchy of machine learning models in order to generate a treatment plan for users experiencing one or more mental health disorders manifesting as cognitive distortions. The machine learning hierarchy provides multiple stages of machine learning, where the outputs of one stage are used as an input for another stage. In a further embodiment, a first stage includes application of a cognitive distortions model and a task performance model. The outputs of those models are used, among other features, as features to be input to a digital therapeutics recommendation model during the second stage. The hierarchy provides more accurate models at each subsequent stage, thereby resulting in a more accurate model for generating treatment plans than a model trained based on the various inputs in one stage.

In another embodiment, additional machine learning models may be trained for aspects of treatment in addition to the digital therapeutics exercise task digital therapeutics. Such additional aspects of treatment may include, but are not limited to, prescribing group therapy, formal and informal peer support, prescribing virtual reality sessions, prescribing pharmaceuticals, or a combination thereof in tandem with the digital therapeutics.

The treatment plan created based on the outputs of the machine learning models described above effectively serves as an intervention curriculum including a set of interventions designed to improve mental health within a peer support setting. The set of interventions may further include a multi-faceted set of interventions providing various means of engagement. Each intervention is an assigned exercise designed to allow for addressing mental health individually and within a group. The treatment plan is created based on a set of exercises targeted toward a specific goal. Relevant actions for a particular user are determined using the machine learning models noted above based on the engagement and needs of those users.

FIG. 1 shows an example network diagram 100 utilized to describe the various disclosed embodiments. In the example network diagram 100, a user device 120, a digital therapeutics treatment system 130, and a plurality of databases 140-1 through 140-N (hereinafter referred to individually as a database 140 and collectively as databases 140, merely for simplicity purposes) are communicatively connected via a network 110.

The network 110 may be, but is not limited to, a wireless, cellular or wired network, a local area network (LAN), a wide area network (WAN), a metro area network (MAN), the Internet, the worldwide web (WWWW), similar networks, and any combination thereof.

The user device (UD) 120 may be, but is not limited to, a personal computer, a laptop, a tablet computer, a smartphone, a wearable computing device, or any other device capable of receiving and displaying data related to digital therapeutics. In an example implementation, the user device 120 includes one or more input/output (I/O) devices 125. The I/O devices 125 are configured to provide a user interface for providing digital therapeutics to the user (e.g., via display of prescribed digital therapeutics exercises and confirmation of completion by the user).

The user device 120 may also be utilized for interactions of a user with a digital therapeutics platform implemented by one or more servers 150. To this end, the user device 120 may have installed thereon a software application (app) 127. The digital therapeutics platform may be a social media platform connecting users including the user of the user device 120. User content data may include user content such as posts, responses, messages (e.g., chat messages), and other content uploaded to or otherwise stored in the social media platform.

The digital therapeutics treatment system 130 is configured to at least determine treatments using machine learning as described herein. In some embodiments, the digital therapeutics treatment system 130 is further configured to send content for display on the user device 120 as part of administration of the digital therapeutics treatment.

It should be noted that FIG. 1 merely shows an example environment in which the disclosed techniques may be implemented, but that the disclosed embodiments are not restricted to the network diagram shown in FIG. 1. In particular, in some implementations, at least some of the techniques described herein may be performed by the user device 120. For example, instructions for performing at least some of the disclosed embodiments (e.g., embodiments including applying machine learning models) may be implemented via the software application 127). This may be useful, for example, in order to ensure privacy by processing data and determining diagnoses locally on the user device 120. In addition, the administration of treatment techniques described herein may, in some implementations, be performed by a doctor.

Figure 2:
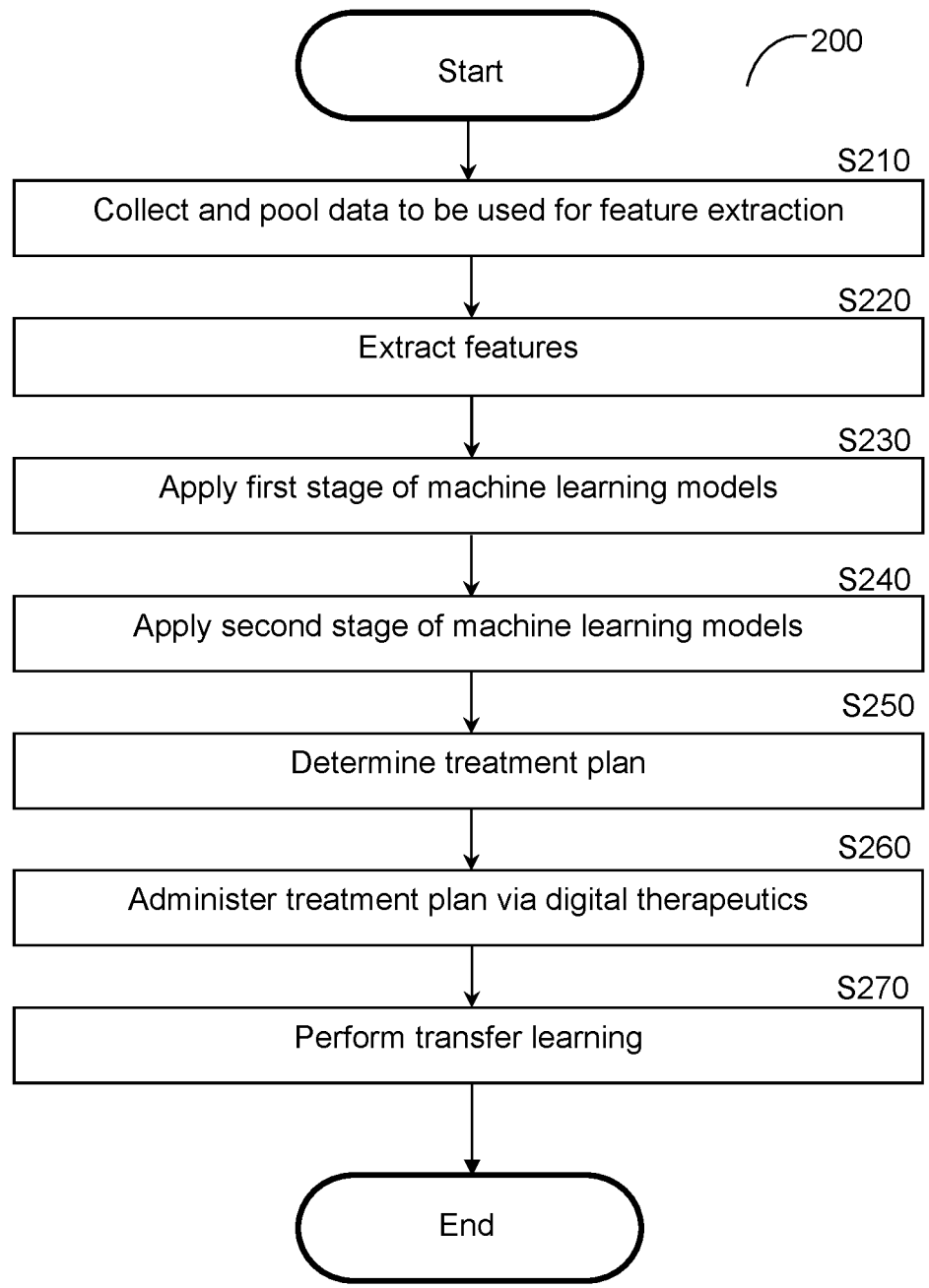
FIG. 2 is a flowchart illustrating a method for treating mental health disorders using machine learning according to an embodiment.

FIG. 2 is a flowchart 200 illustrating a method for treating mental health disorders using machine learning according to an embodiment. In an embodiment, the method is performed by the digital therapeutics system 130, FIG. 1. In another embodiment, the method is performed by the user device 120, FIG. 1.

At optional S210, data related to a user is collected. In an embodiment, the collected data includes at least data related to user-created content platforms (e.g., social media platforms) such as, but not limited to, a mental health disorder treatment platform, open source Internet forums, other open source language models, or a combination thereof. In a further embodiment, the collected data may further include data related to other users (e.g., other users of the same platforms from which the user-related data is collected).

At S220, features are extracted from the data related to a user. The data related to a user at least includes content created by the user. In an embodiment, such content includes textual content such as posts, responses, messages, and the like. In an example implementation, such content is content provided via a social media platform.

In an embodiment, the extraction of features may further include deriving features by applying artificial neural networks as part of deep learning. In particular, language-based features derived from content created by the user (e.g., posts, comments, replies, social media participation such as "ask me anything" threads, and chat messages) may be derived at least partially using deep learning. This derivation of language-based features using deep learning allows for more accurate and more precise extraction of features from natural language, which in turn improves the results of the subsequent machine learning stages.

At S230, a first stage of machine learning is applied to at least a first portion of the extracted features. In an embodiment, S230 at least includes identification of cognitive distortions of the user via a cognitive distortion model. Such identification may further indicate a score or other representation of a degree of severity for the mental health disorder. In a further embodiment, S230 may further include determining task performance for tasks previously performed by the user via a task performance model. Each of the cognitive distortion model and the task performance model is trained based on respective training features.

In an embodiment, the first stage of machine learning may be at least partially implemented using classifiers. In particular, the cognitive distortions model may classify data into one or more potential mental health disorders of the user.

At S240, a second stage of machine learning is applied to at least a second portion of the extracted features and the outputs of the first stage of machine learning. In an embodiment, S230 at least includes determination of parameters for a treatment plan for the user via a task recommender model. The treatment plan includes digital therapeutics exercise tasks to be prescribed to the user, and may further include types of tasks, specific tasks, acuity level of the user for different tasks, or a combination thereof.

In some embodiments, transfer learning may be utilized in order to improve the second machine learning model based on results of training a task recommender model for a group of other users. To this end, a task recommender model may be pre-trained based on data related to the other users of the group of other users, and the pre-trained task recommender model may be used as the starting model for training of what will become the task recommender model for the user.

In a further embodiment S240 may also include determining parameters for a conversational agent interacting with the user during treatment using a conversational parameters model and reconfiguring the conversational agent based on the determined parameters. Each of the task recommender model and the conversational parameters model is trained based on respective training features.

In an embodiment, the second stage of machine learning may be at least partially implemented using classifiers. In particular, the task recommender model may classify tasks to be prescribed as treatment into types of tasks that are suitable for the user.

At S250, based on the output of the second stage of machine learning, a treatment plan is determined. In an embodiment, the treatment plan is a digital therapeutics treatment plan including assigning, to the user, digital therapeutics exercise tasks via a user device (e.g., the user device 120, FIG. 1).

In an embodiment, S250 includes identifying the task types (e.g., based on a task identifier output during the second stage of machine learning) in a task database, adding the context of the user's challenges to the task (e.g., based on prior task performance), determining the tasks based on the identified task types, adding the tasks to a user's task queue, and optionally adding the task to similar users' queue. Similar users may be, but are not limited to, users having similar mental health disorders (e.g., users having scores for the same mental health disorders above a threshold).

At optional S260, the treatment plan is administered to the user via digital therapeutics. The treatment plan may be administered via a user device which may be configured to, but is not limited to, displaying instructions for performing the digital therapeutics exercise tasks, receiving confirmation of performance of tasks, receiving additional content based on tasks, combinations thereof, and the like. Such additional content may include, but is not limited to, posts, comments, likes, dislikes, multimedia content, or other user-created content provided as part of or in response to the treatment plan or a portion thereof.

At optional S270, based on the additional content received during administration of the treatment plan, the machine learning models may be trained further. To this end, transfer learning techniques may be utilized to improve the models based on the user's feedback as indicated in the additional content. More specifically, the natural language and other expressions of behaviors indicated in the additional content are used as feedback to one or more of the machine learning models (e.g., the cognitive distortion model, the task recommender model, or both), and the resulting models may be used for another user or group of users. In particular, features may be derived as discussed above based on data indicating a user's progress with digital therapeutics and content generated in response to digital therapeutics. This, in turn, may alter the types and scores of cognitive distortions determined for the user.

In this regard, it is noted that transfer learning is a research problem focusing on using knowledge gained while solving one problem and applying that knowledge to a different but related problem. Different users have unique mental health disorders but that related mental health disorders that manifest similarly can be utilized to learn more effective forms of treatment for other users. Accordingly, transfer learning can be utilized to improve the accuracy of machine learning models trained to, for example, determining digital therapeutics exercise tasks.

In a further embodiment, the transfer learning techniques may be utilized to train the models in order to provide better treatment plans for similar groups of users. The task recommender model may be trained based on features extracted from the additional content generated by multiple users in the same peer group on any platform in order to train the task recommender model to provide recommendations that will improve the mental well-being of the group via collective participation. To this end, when training the task recommender for another user or group of users, the model trained for the first group of users is utilized as the starting model for training such that the results of training the model for the first group of users can be used to improve the training of the task recommender model for a different user or group of users. The other user or group of users may be a user or group of users having one or more common attributes such as, but not limited to, occupation, title, similar cognitive distortions, combinations thereof, and the like.

It should be noted that different features are used for different machine learning models and during different stages of machine learning. The disclosed embodiments are not limited to the particular flow shown in FIG. 2 with respect to extraction of features. Features may be extracted in a different order from each other, at least some features may be extracted during or after application of one of the machine learning models. In particular, features not needed for one stage of machine learning or for one machine learning model may be extracted during or after that stage or model without departing from the scope of the disclosure.

Figure 3:
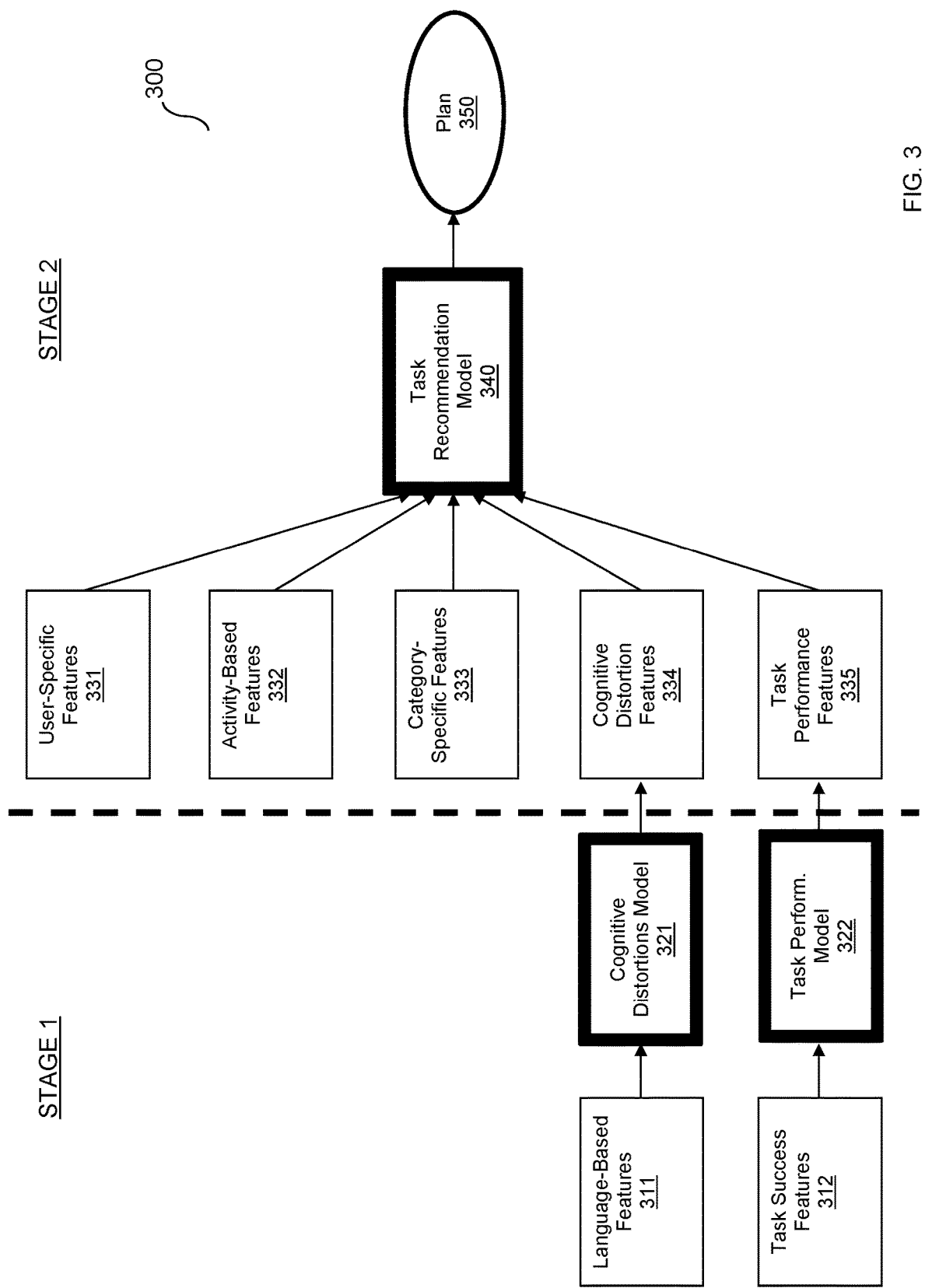
FIG. 3 is a flow diagram illustrating a machine learning hierarchy according to an embodiment.

FIG. 3 is a flow diagram 300 illustrating a machine learning hierarchy according to an embodiment.

As depicted in FIG. 3, during a first stage of machine learning, language-based features 311 are input to a cognitive distortions model 321 in order to output cognitive distortion features 334. Likewise, task success features 312 are input to a task performance ("perform.") model 322 in order to output task performance features 335.

During a second stage of machine learning, the cognitive distortion features 334 and the task performance features 335 are input to the task recommendation model 340 along with other features in order to output data related to a plan 350. The plan 350 includes data to be used in formulating a treatment plan including, but not limited to, types of tasks to be assigned to the user, task identifiers of tasks to be assigned to the user, acuity level of the user, or a combination thereof. In the embodiment shown in FIG. 3, the other features include user-specific features 331, activity-based features 332, and category-specific features 333. Further descriptions and examples of each type of feature used in FIG. 3 is described further below with respect to FIG. 4.

In some embodiments, the task recommender model 340 or another machine learning model (not shown in FIG. 3) may be further configured to output parameters to be used by a conversational agent that will interact with the user during treatment. To this end, inputs for such machine learning of conversational parameters may include, but are not limited to, the language-based features 311, meta language-based features (not shown in FIG. 3), features indicating challenges identified by the user in conversation (e.g., features extracted by analyzing messages of the user for challenge-based terminology), and historical user response features. The output conversational parameters may include, but are not limited to, empathy tone, response type, and response content (e.g., text or other specific content to include).

Figure 4:
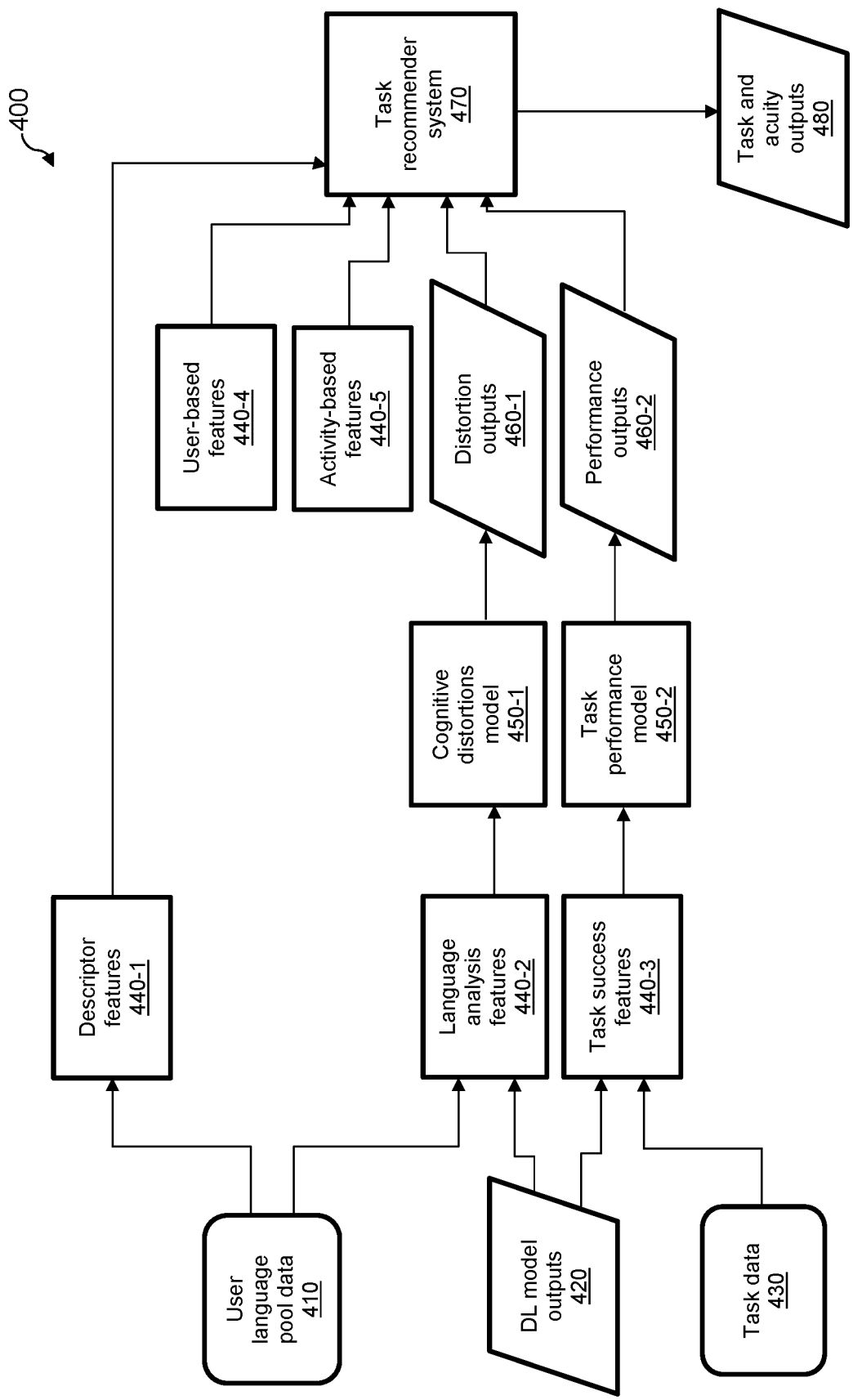
FIG. 4 is a flow diagram illustrating a machine learning schema according to an embodiment.

FIG. 4 is a flow diagram 400 illustrating a machine learning schema according to an embodiment.

In the embodiment shown in FIG. 4, data including user language pool data 410, meta language-based features 420 output by deep learning (DL) models are used to derive features (DL model outputs 420), task data 430 including prior task results and identifiers. The derived features include and task category-specific language descriptor features 440-1, language analysis features 440-2 (e.g., linguistic inquiry types and word counts), and task success features 440-3. The user language pool data 410 may include, but is not limited to, posts, comments, replies, and chat data. meta language-based features include outputs of a deep learning model such as, but not limited to, sentiment analysis, named entity recognition, topic identification, and tokenization.

The language analysis features 440-2 shown in FIG. 4 may include linguistic inquiry types, word counts, and deep learning features (e.g., weights of convolutional and recurrent neural networks). The language analysis features 440-2 are input to a cognitive distortions model 450-1, which is a machine learning model trained based on historical language analysis features. The cognitive distortions model 450-1 outputs types of cognitive distortions and corresponding strength values indicating the degree to which the user exhibits each respective type of cognitive distortion.

The task success features 440-3 are defined separately for different tasks. The task success features 440-3 are input to a task performance model trained based on historical task success features. The task performance model 450-2 outputs performance scores indicating a degree of success on previous tasks.

The cognitive distortions outputs 460-1 and task performance outputs 460-2 are input as features to a machine learning model of a task recommender system 470. The task recommender system 470 outputs data related to digital therapeutics exercise tasks to be prescribed to a user as part of treating the user's cognitive distortions in the form of task and acuity outputs 480. In the implementation shown in FIG. 4, such outputs 480 include the type of each task suitable for the user, task types and identifiers of tasks enjoyed by the user, and acuity level for each task. Other input features for the task recommender system include user-specific variation features, activity-based features, and the task category-specific language descriptors.

In some embodiments (not shown in FIG. 4), the task recommender system 470 may further output parameters (not shown) to be used for a conversational agent interacting with the user based at least partially on the features discussed with respect to FIG. 4. Examples for such output are described above in the discussion of FIG. 3.

The user-based features 440-4 may include user-specific variation features such as, but not limited to, user preferences (i.e., preferences of the current user), user-specific features of other users, and task type and identification data. The activity-based features 440-5 may include, but are not limited to, a number of tasks completed, an amount of time spent completing each task, a number of clinical assessments completed, clinical assessment scores for the completed clinical assessments, and task types and identifiers of prior tasks.

Figure 5:
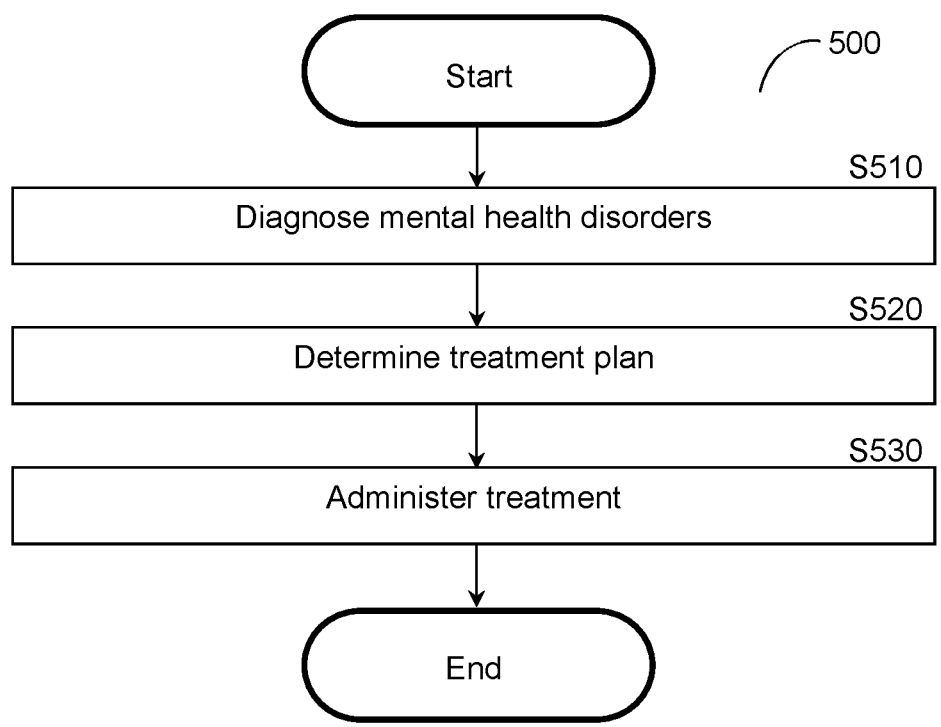
FIG. 5 is a flowchart illustrating a method of treating target mental health disorders using digital therapeutics according to an embodiment.

FIG. 5 is a flowchart 500 illustrating a method of treating mental health disorders according to an embodiment.

At optional S510, one or more mental health disorders of a patient are diagnosed. The diagnosis may be based on clinical evaluation of the patient, analysis of content created by the patient (e.g., content uploaded to a social media platform), or a combination thereof. In an alternative embodiment, the diagnosis may be predetermined.

In an embodiment, S510 may include applying one or more machine learning models, for example as described above. Cognitive distortions of the patient are identified. The combination of cognitive distortions of the patient symptomize the mental health disorders of the patient. In a further embodiment, the mental health disorders may have corresponding scores, and the patient is diagnosed with only mental health disorders based on cognitive distortions having scores above a threshold (i.e., mental health disorders which have been determined to be likely applicable to the patient).

At S520, a treatment plan is determined based on the mental health disorders of the patient. In an embodiment, the treatment plan includes one or more digital therapeutics exercise tasks. Each digital therapeutics exercise task belongs to a category of digital therapeutics tasks corresponding to a type of mental health disorder among the diagnosed mental health disorders. In a further embodiment, the treatment plan is determined based on clinical assessment scores of the user from previous tasks.

In an example implementation, tasks are divided into three broad categories: wellbeing assessments, therapy exercises, and community engagement. In an embodiment, the task exercise categories for corresponding types of target mental health disorders are assigned as illustrated in Table 1:

TABLE 1

| Mental health disorder | Category of Task |
| --- | --- |
| Depression | Strengths identification |
| Anxiety | Mood identification |
| Substance use disorder | Compassion |
| Mood and personality disorders | Savoring |
| Depression, anxiety, and substance use disorder | Cognitive restructuring |
| Depression, anxiety, and substance use disorder | Behavioral activation |
| Substance user disorder | Gratitude |

Alternatively or collectively, the criteria for assigned tasks may be specific mental health disorders or combinations of types of mental health disorders and severities (e.g., as represented by a score indicating the degree of the mental health disorder). Further, the specific tasks to be assigned may be selected from among tasks belonging to the corresponding category based on factors such as, but not limited to, specific mental health disorders, severity of mental health disorder, prior tasks completed by the patients, tasks completed by other patients, combinations thereof, and the like.

In another embodiment, the treatment plan includes a set of digital therapeutics exercise tasks to be administered to the patient. The set may include multiple instances of any or all of the digital therapeutics exercise tasks, and the digital therapeutics exercise tasks may further be arranged in a particular order. As a non-limiting example the set may involve performing a first digital therapeutics exercise task, a second digital therapeutics exercise task, the first digital therapeutics exercise task again, and a third digital therapeutics exercise task. In a further embodiment, the treatment plan may be implemented via digital therapeutics, for example via a software application installed on a user device.

In yet another embodiment, the treatment plan may further include one or more supplemental prescriptions. The supplemental prescriptions may include, but are not limited to, treatment via a doctor (e.g., a psychiatrist), additional social interaction (e.g., via a social media platform), and the like. In an example implementation, the additional social interaction includes sharing the prescribed digital therapeutics exercise tasks with a community of the patient's peers, participating in the peer community by providing self-generated content (e.g., questions and comments), participating in group therapy or coaching sessions, a combination thereof and the like.

At S530, treatment is administered. The administration at least includes prescribing the treatment plan to the patient. In some implementations, the treatment plan may be administered via a user device (e.g., the user device 120, FIG. 1).

A non-limiting example treatment plan follows. This example treatment plan may be a default treatment plan that is modified based on determinations described above based on mental health disorders exhibited by a patient. The example treatment plan includes prescription of a series of digital therapeutics exercise tasks over a period of weeks. The tasks are given descriptions indicating the activities to be undertaken by the user to complete the tasks as well as explanations of evidence supporting assignment of those particular tasks and suggested community channels to be used for providing user-created content in response to the task assignments.

Week 0 (Initial Assessment)
Task 1:
  Estimated completion time: 2 minutes
  Task title: Finish your wellbeing assessment
  Task description: You can only improve what you can measure.
  Task evidence: Over 50 peer-reviewed studies have shown that people who measured their wellbeing using a clinical-grade scale like PHQ8 were more aware of their wellbeing needs and experienced faster improvements in their wellbeing compared to people who did not.
Week 1
Task 1:
  Estimated completion time: 3 minutes
  Task title: Reinforce your strengths
  Task description: Recollect an activity or a thought process that has supported your wellbeing and share in detail with your community.
  Task evidence: Identifying what has helped your wellbeing makes repeating the behavior easier. This is an evidence-based practice for building resilience. This technique is a part of solution-focused therapy. Over 70 peer-reviewed studies have demonstrated its effectiveness in addressing a spectrum of wellbeing challenges including depression and substance use disorder.
  Suggested channels: Aware gym, Depression, Substance Use Disorder
Task 2:
  Estimated completion time: 3 minutes
  Task title: Outline your strengths
  Task description: Recollect an activity or a thought process that you have tried but has NOT worked for your wellbeing and share in detail with your community.
  Task evidence: Identifying what has not worked for you helps you outline your current strengths better and also makes avoiding those behaviors easier. Research has shown that clearly outlining your strengths can help you access them easily when you need them.
  Suggested channels: Aware gym, Depression, Substance Use Disorder
Week 2
Task 1:
  Estimated completion time: 2 minutes
  Task title: Rate your mood
  Task description: Take a moment to breathe. Identify how you are feeling. Rate your mood from 0-10 (10 being the highest experience of that mood). Share this in detail with your community.
  Task evidence: Identifying and rating how you feel helps improve emotional intelligence. This can help improve relations with peers and clients. This technique is an integral part of Cognitive Behavior Therapy, which is an evidence-based wellbeing practice supported by over 500 research articles.
  Suggested channels: Aware gym, Depression, Anxiety
Task 2:
  Estimated completion time: 3 minutes
  Task title: Experience compassion
  Task description: Find a post on the community on your topic of interest and comment on it.
  Task evidence: Supporting others has therapeutic benefits. Research has shown that compassion can serve as a buffer against stress by protecting us from stress. In addition, the "pleasure centers" of the brain which help us experience pleasure (e.g. food, sex, money) are also equally activated by acts of compassion. Finally, increased compassion is associated with decreased risk of depression.
  Suggested channels: Aware gym, Depression, Substance Use Disorder
Week 3
Task 1:
  Estimated completion time: 2 minutes
  Task title: Spot exceptions
  Task description: Recollect an overwhelming obstacle that you have faced in the past. When faced with this obstacle, what's your "go to" way to overcome it? Share this in detail with your community.
  Task evidence: Spotting positive exceptions from the past can help overcome challenges in the future. Exception finding is designed to build long-term resilience, and is an integral part of solution-focused therapy. Over 70 peer-reviewed studies have demonstrated the effectiveness of this therapy in addressing a spectrum of wellbeing challenges including depression and substance use disorder.
  Suggested channels: Aware gym, Depression, Anxiety
Task 2:
  Estimated completion time: 3 minutes
  Task title: Savor an experience.
  Task description: Recollect a positive experience you had in the past week and how it made you feel. Can you rate your feeling from 0-10 (10 being the highest experience of that mood)? Share this in detail with your community.
  Task evidence: Savoring positive experiences helps to upregulate positive emotions. Savoring is the opposite of coping and is a part of Positive Psychotherapy. Research has shown that savoring can boost creativity, help build stronger relationships, and decrease depressive symptoms.
Week 4:
Task 1:
  Estimated completion time: 3 minutes
  Task title: Practice self-compassion
  Task description: What did you say to yourself when the last time you were self-critical? Think about what you would say to a loved one in the same situation. Now use these words to rephrase what you say to yourself. Share this in detail with your community.
  Task evidence: Self-compassion has several therapeutic and occupational benefits. Research has shown that self-compassion is associated with improved conscientiousness, leadership, and resilience as well as decreased symptoms of stress, depression, and anxiety. Self-compassion practices are often integrated into Positive Psychotherapy and Acceptance and Commitment Therapy.
Task 2:
  Estimated completion time: 3 minutes
  Task title: Decatastrophize
  Task description: Recollect a situation you are fearful or anxious about. Describe the worst case, best case, and most likely case scenario outcome. Reflect on your findings. Share this in detail with your community.
  Task evidence: Decatastrophizing helps to effectively overcome worries. It is a technique rooted in Cognitive Behavioral Therapy, which is an evidence-based technique found to be most effective in overcoming fears and anxiety.

Week 5
Task 1:
  Estimated completion time: 4 minutes
  Task title: Identify behavioral activations
  Task description: Take a moment to notice your mood this week. Compare it to your mood last week. Can you remember anything you did that either positively or negatively affected your mood? Please share in detail with your community.
  Task evidence: Understanding how your mood is related to your behavior and vice-versa can help better manage mood using the appropriate behaviors. Research has shown that this technique, known as behavioral activation, can be very effective in overcoming several wellbeing challenges, including depression.
Task 2:
  Estimated completion time: 4 minutes
  Task title: Try gratitude
  Task description: Take a moment to remember one blessing that you have. How has this helped you? Please share in detail with your community.
  Task evidence: Gratitude can be very therapeutic. Research has shown that it improves confidence, patience, and provides a buffer from stress and depression. Gratitude is generally integrated into Positive Psychotherapy.

Figure 6:
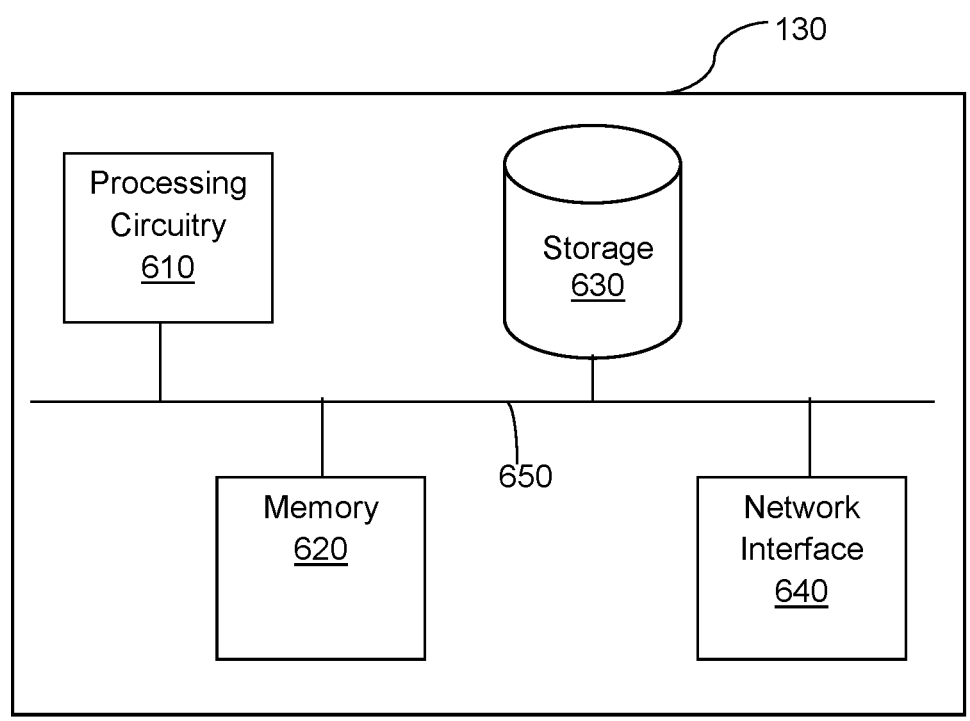
FIG. 6 is a schematic diagram of a treatment system according to an embodiment.

FIG. 6 is an example schematic diagram of a digital therapeutics treatment system 130 according to an embodiment. The digital therapeutics treatment system 130 includes a processing circuitry 610 coupled to a memory 620, a storage 630, and a network interface 640. In an embodiment, the components of the digital therapeutics treatment system 130 may be communicatively connected via a bus 650.

The processing circuitry 610 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 620 may be volatile (e.g., random access memory, etc.), non-volatile (e.g., read only memory, flash memory, etc.), or a combination thereof.

In one configuration, software for implementing one or more embodiments disclosed herein may be stored in the storage 630. In another configuration, the memory 620 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 610, cause the processing circuitry 610 to perform the various processes described herein.

The storage 630 may be magnetic storage, optical storage, and the like, and may be realized, for example, as flash memory or other memory technology, compact disk-read only memory (CD-ROM), Digital Versatile Disks (DVDs), or any other medium which can be used to store the desired information.

The network interface 640 allows the digital therapeutics treatment system 130 to communicate with the databases 140 for the purpose of, for example, retrieving data user preference data, retrieving data related to prior tasks of users, and the like. Further, the network interface 640 allows the digital therapeutics treatment system 130 to communicate with the user device 120 for the purpose of sending data to be displayed on the user device 120 in order to prescribe and have the user complete digital therapeutics digital therapeutics exercise tasks.

It should be understood that the embodiments described herein are not limited to the specific architecture illustrated in FIG. 6, and other architectures may be equally used without departing from the scope of the disclosed embodiments.

It should also be noted that, at least in some implementations, at least some techniques described herein may be performed via the user device. As a particular example, machine learning models may be stored in the user device 120 after training and applied by the user device 120. To this end, the user device 120 may include any or all of the components of FIG. 6 in order to allow for this functionality. Applying the machine learning models locally on the user device may aid in complying with medical privacy regulations.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for treating mental health disorders using digital therapeutics, comprising:
    training a task recommender machine learning model using a training set including training cognitive distortion features and training task performance features for at least one user, wherein the training cognitive distortion features includes types of cognitive distortions and cognitive distortion degrees of cognitive distortions exhibited by the at least one user;
    identifying a plurality of cognitive distortions of a patient, wherein identifying the plurality of cognitive distortions of the patient further comprises applying a cognitive distortions machine learning model to a portion of features extracted from data related to the patient including language data and digital behavior data, wherein the cognitive distortions machine learning model is trained using training user-created content created by the user, wherein the cognitive distortions machine learning model outputs a plurality of cognitive distortion types and a plurality of cognitive distortion degrees of the plurality of cognitive distortions when applied to the portion of features extracted from the data related to the patient, wherein at least one mental health disorder of the patient is symptomized by a combination of cognitive distortions among the identified plurality of cognitive distortions of the patient;
    determining a plurality of digital therapeutics exercise tasks for the patient, wherein determining the plurality of digital therapeutics exercise tasks for the patient further comprises applying the task recommender machine learning model to a portion of application task performance features for the patient and to cognitive distortion features including the plurality of cognitive distortion types output by the cognitive distortions machine learning model and the plurality of cognitive distortion degrees output by the cognitive distortions machine learning model;
    determining a treatment plan for the patient based on at least one mental health disorder of the patient, wherein the treatment plan includes the plurality of digital therapeutics exercise tasks, wherein each digital therapeutics exercise task is selected from among a category of digital therapeutics exercise tasks corresponding to a type of mental health disorder of the at least one mental health disorder of the patient; and
    administering treatment to the patient by prescribing the treatment plan to the patient and sending data for administering the treatment plan to a user device of the patient, wherein administering the treatment further comprises assigning the plurality of digital therapeutics exercise tasks to the patient via a user interface of a user device operated by the patient.

2. The method of claim 1, further comprising:
    diagnosing the patient with the at least one mental health disorder by applying at least one machine learning model to data including user-generated content created by the patient.

3. The method of claim 1, wherein the cognitive distortion features to which the task recommender model is applied are based on output of the cognitive distortions machine learning model.

4. The method of claim 3, wherein the at least one user is at least one first user, further comprising:
    pre-training the task recommender machine learning model based on features extracted from training data related to at least one second user in order to create a pre-trained machine learning model for transfer learning; and
    training the task recommender machine learning model using the pre-trained model as the starting model.

5. The method of claim 3, further comprising:
    identifying a plurality of task types based on output of the task recommender machine learning model, wherein the plurality of digital therapeutics exercise tasks is determined based on the identified plurality of task types; and
    creating a task queue for the user, wherein the task queue includes the plurality of digital therapeutics exercise tasks.

6. The method of claim 1, wherein the plurality of digital therapeutics exercise tasks is determined based further on a severity of each of the at least one mental health disorder of the patient.

7. The method of claim 1, wherein each category of digital therapeutics exercise tasks is any of: wellbeing assessments, therapy exercises, reflections, articles, workshops, and community engagement.

8. The method of claim 1, wherein the at least one user is at least one first user, wherein the plurality of digital therapeutics exercise tasks is determined by applying at least one machine learning model to data collected from at least one second user sharing at least one common attribute with the patient, wherein the data collected from the at least one second user sharing at least one common attribute with the patient includes language data and digital behavior data.

9. The method of claim 1, wherein the at least one mental health disorder of the patient includes a first mental health disorder, wherein the first mental health disorder is depression, wherein a first digital therapeutics exercise task of the plurality of digital therapeutics exercise tasks corresponds to the first mental health disorder, wherein the category from which the first digital therapeutics exercise task is selected is a strengths identification category.

10. The method of claim 1, wherein the at least one mental health disorder of the patient includes a first mental health disorder, wherein the first mental health disorder is anxiety, wherein a first digital therapeutics exercise task of the plurality of digital therapeutics exercise tasks corresponds to the first mental health disorder, wherein the category from which the first digital therapeutics exercise task is selected is a mood identification category.

11. The method of claim 1, wherein the at least one mental health disorder of the patient includes a first mental health disorder, wherein the first mental health disorder is substance use disorder, wherein a first digital therapeutics exercise task of the plurality of digital therapeutics exercise tasks corresponds to the first mental health disorder, wherein the category from which the first digital therapeutics exercise task is selected is a compassion category.

12. The method of claim 11, wherein the at least one mental health disorder of the patient further includes a second mental health disorder, wherein the second mental health disorder is substance use disorder, wherein a second digital therapeutics exercise task of the plurality of digital therapeutics exercise tasks corresponds to the second mental health disorder, wherein the category from which the second digital therapeutics exercise task is selected is a gratitude category.

13. The method of claim 1, wherein the at least one mental health disorder of the patient includes a first mental health disorder, wherein the first mental health disorder is mood and personality disorder, wherein a first digital therapeutics exercise task of the plurality of digital therapeutics exercise tasks corresponds to the first mental health disorder, wherein the category from which the first digital therapeutics exercise task is selected is a savoring category.

14. The method of claim 1, wherein the at least one mental health disorder of the patient includes a first mental health disorder, a second mental health disorder, and a third mental health disorder; wherein the first mental health disorder is depression, the second mental health disorder is anxiety, and the third mental health disorder is substance use disorder; wherein a first digital therapeutics exercise task of the plurality of digital therapeutics exercise tasks corresponds to a combination of the first mental health disorder, the second mental health disorder, and the third mental health disorder; wherein the category from which the first digital therapeutics exercise task is selected is a cognitive restructuring category.

15. The method of claim 1, wherein the at least one mental health disorder of the patient includes a first mental health disorder, a second mental health disorder, and a third mental health disorder; wherein the first mental health disorder is depression, the second mental health disorder is anxiety, and the third mental health disorder is substance use disorder; wherein a first digital therapeutics exercise task of the plurality of digital therapeutics exercise tasks corresponds to a combination of the first mental health disorder, the second mental health disorder, and the third mental health disorder; wherein the category from which the first digital therapeutics exercise task is selected is a behavioral activation category.

16. The method of claim 1, wherein the at least one mental health disorder is at least one of depression, anxiety, substance use disorder, and mood and personality disorder; wherein each task of the plurality of tasks is selected from a strengths identification category when the at least one mental health disorder is depression; wherein each task of the plurality of tasks is selected from a mood identification category when the at least one mental health disorder is anxiety; wherein each task of the plurality of tasks is selected from a compassion category when the at least one mental health disorder is substance use disorder; wherein each task of the plurality of tasks is selected from a savoring category when the at least one mental health disorder is mood and personality disorder; wherein each task of the plurality of tasks is selected from a cognitive restructuring category when the at least one mental health disorder is depression, anxiety, and substance use disorder.

17. A non-transitory computer readable medium having stored thereon instructions for causing a processing circuitry to execute a process, the process comprising:
training a task recommender machine learning model using a training set including training cognitive distortion features and training task performance features for at least one user, wherein the training cognitive distortion features includes types of cognitive distortions and cognitive distortion degrees of cognitive distortions exhibited by the at least one user;
identifying a plurality of cognitive distortions of a patient, wherein identifying the plurality of cognitive distortions of the patient further comprises applying a cognitive distortions machine learning model to a portion of features extracted from data related to the patient including language data and digital behavior data, wherein the cognitive distortions machine learning model is trained using training user-created content created by the at least one user, wherein the cognitive distortions machine learning model outputs a plurality of cognitive distortion types and a plurality of cognitive distortion degrees of the plurality of cognitive distortions when applied to the portion of features extracted from the data related to the patient, wherein at least one mental health disorder of the patient is symptomized by a combination of cognitive distortions among the identified plurality of cognitive distortions of the patient;
determining a plurality of digital therapeutics exercise tasks for the patient, wherein determining the plurality of digital therapeutics exercise tasks for the patient further comprises applying the task recommender machine learning model to a portion of application task performance features for the patient and to cognitive distortion features including the plurality of cognitive distortion types output by the cognitive distortions machine learning model and the plurality of cognitive distortion degrees output by the cognitive distortions machine learning model;
determining a treatment plan for the patient based on at least one mental health disorder of the patient, wherein the treatment plan includes the plurality of digital therapeutics exercise tasks, wherein each digital therapeutics exercise task is selected from among a category of digital therapeutics exercise tasks corresponding to a type of mental health disorder of the at least one mental health disorder of the patient; and
administering treatment to the patient by prescribing the treatment plan to the patient and sending data for administering the treatment plan to a user device of the patient, wherein administering the treatment further comprises assigning the plurality of digital therapeutics exercise tasks to the patient via a user interface of a user device operated by the patient.

18. A system for treating mental health disorders using digital therapeutics, comprising:
a processing circuitry; and
a memory, the memory containing instructions that, when executed by the processing circuitry, configure the system to:
train a task recommender machine learning model using a training set including training cognitive distortion features and training task performance features for at least one user, wherein the training cognitive distortion features includes types of cognitive distortions and cognitive distortion degrees of cognitive distortions exhibited by the at least one user;
identify a plurality of cognitive distortions of a patient, wherein identifying the plurality of cognitive distortions of the patient further comprises applying a cognitive distortions machine learning model to a portion of features extracted from data related to the patient including language data and digital behavior data, wherein the cognitive distortions machine learning model is trained using training user-created content created by the at least one user, wherein the cognitive distortions machine learning model outputs a plurality of cognitive distortion types and a plurality of cognitive distortion degrees of the plurality of cognitive distortions when applied to the portion of features extracted from the data related to the patient, wherein at least one mental health disorder of the patient is symptomized by a combination of cognitive distortions among the identified plurality of cognitive distortions of the patient;

determine a plurality of digital therapeutics exercise tasks for the patient, wherein determining the plurality of digital therapeutics exercise tasks for the patient further comprises applying the task recommender machine learning model to a portion of application task performance features for the patient and to cognitive distortion features including the plurality of cognitive distortion types output by the cognitive distortions machine learning model and the plurality of cognitive distortion degrees output by the cognitive distortions machine learning model;

determine a treatment plan for the patient based on at least one mental health disorder of the patient, wherein the treatment plan includes the plurality of digital therapeutics exercise tasks, wherein each digital therapeutics exercise task is selected from among a category of digital therapeutics exercise tasks corresponding to a type of mental health disorder of the at least one mental health disorder of the patient; and administer treatment to the patient by prescribing the treatment plan to the patient and sending data for administering the treatment plan to a user device of the patient, wherein administering the treatment further comprises assigning the plurality of digital therapeutics exercise tasks to the patient via a user interface of a user device operated by the patient.

* * * * *